US00PP33883P3

(12) United States Plant Patent
Schoone

(10) Patent No.: US PP33,883 P3
(45) Date of Patent: Jan. 18, 2022

(54) **X *DORITAENOPSIS* PLANT NAMED 'FRUIT PUNCH'**

(50) Latin Name: ***x Doritaenopsis (Doritis* x *Phalaenopsis)***
Varietal Denomination: Fruit Punch

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/340,013

(22) Filed: Jun. 5, 2021

(65) Prior Publication Data

US 2021/0386001 P1 Dec. 9, 2021

Related U.S. Application Data

(60) Provisional application No. 62/705,005, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Doritaenopsis* plant named 'Fruit Punch', characterized by its compact and upright plant habit; moderately vigorous growth habit; strong leaves; strong flowering stems; freely flowering habit with typically two inflorescences per plant, each inflorescence with numerous flowers; purplish red-colored flowers with greenish yellow-colored margins; and good postproduction longevity.

2 Drawing Sheets

Figure 1:
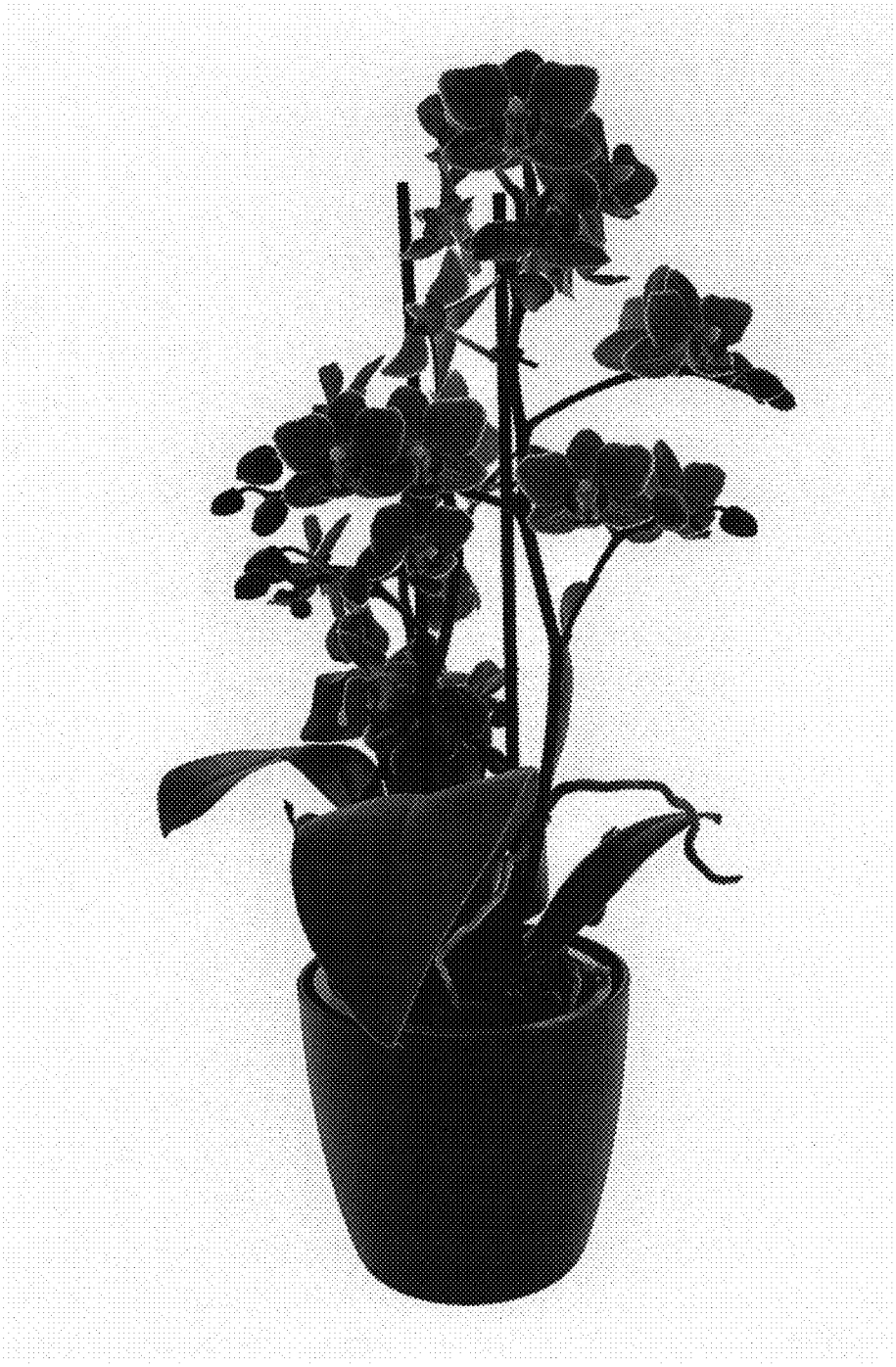

Botanical designation: x *Doritaenopsis* (*Doritis* x *Phalaenopsis*).

Cultivar denomination: 'FRUIT PUNCH'.

CROSS-REFERENCED TO CLOSELY-RELATED APPLICATIONS

Title: Varieties of *Doritaenopsis* Plants
Inventor: René Schoone
Filed: Jun. 6, 2020
Ser. No. 62/705,005
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0824. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of x *Doritaenopsis* plant, botanically known as x *Doritaenopsis* (*Doritis* x *Phalaenopsis*), commonly referred to as *Doritaenopsis* and hereinafter referred to by the name 'Fruit Punch'.

The new *Doritaenopsis* plant is a product of a planned breeding program conducted by the Inventor in Nantou, Taiwan and Heemskerk, The Netherlands. The objective of the breeding program is to develop new fast-growing and freely flowering *Doritaenopsis* plants with good leaf shape and large flowers with unique and attractive patterns and coloration.

The new *Doritaenopsis* plant originated from a cross-pollination in February, 2008 in Nantou, Taiwan of x *Doritaenopsis* 'Sweet Strawberry', not patented, as the female, or seed, parent with x *Doritaenopsis* 'Sunrise Red Peoker', not patented, as the male, or pollen, parent. The new *Doritaenopsis* plant was discovered and selected by the Inventor as a single flowering plant from within the progeny of the stated cross-pollination grown in a controlled greenhouse environment in Heemskerk, The Netherlands in February, 2018.

Asexual reproduction of the new *Doritaenopsis* plant by in vitro meristem propagation in a controlled environment in Assendelft, The Netherlands since February, 2019 has shown that the unique features of this new *Doritaenopsis* plant are stable and reproduced true to type in successive generations.

SUMMARY OF THE INVENTION

Plants of the new *Doritaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fruit Punch'. These characteristics in combination distinguish 'Fruit Punch' as a new and distinct *Doritaenopsis* plant:

1. Compact and upright plant habit.
2. Moderately vigorous growth habit.
3. Strong leaves.
4. Strong flowering stems.
5. Freely flowering habit with typically two inflorescences per plant, each inflorescence with numerous flowers.
6. Purplish red-colored flowers with greenish yellow-colored margins.
7. Good postproduction longevity.

Plants of the new *Doritaenopsis* can be compared to plants of the female parent, 'Sweet Strawberry'. Plants of the new *Doritaenopsis* differ primarily from plants of 'Sweet Strawberry' in flower color as plants of the new *Doritaenopsis* have purplish red-colored flowers with greenish yellow-colored margins whereas plants of 'Sweet Strawberry' have red purple-colored flowers without a contrasting colored margin.

Plants of the new *Doritaenopsis* can be compared to plants of the male parent, 'Sunrise Red Peoker'. Plants of the new *Doritaenopsis* differ primarily from plants of 'Sunrise Red Peoker' in flower color as plants of the new *Doritaenopsis* have purplish red-colored flowers with greenish yellow-colored margins whereas plants of 'Sunrise Red Peoker' have dark purple-colored flowers without a contrasting colored margin.

Plants of the new *Doritaenopsis* can be compared to plants of x *Doritaenopsis* (*Doritis* x *Phalaenopsis*) 'Secret Fragrance', not patented. In side-by-side comparisons, plants of the new *Doritaenopsis* differ primarily from plants of 'Secret Fragrance' in flower color as plants of the new *Doritaenopsis* have purplish red-colored flowers with greenish yellow-colored margins whereas plants of 'Secret Fragrance' have violet-colored flowers without a contrasting colored margin.

BRIEF DESCRIPTION OF THE PHOTOGRAPHS

The accompanying photographs illustrate the overall appearance of the new *Doritaenopsis* plant showing the colors as true as it is reasonably possible to obtain in colored reproductions of this type. Colors in the photographs may differ slightly from the color values cited in the detailed botanical description which accurately describe the colors of the new *Doritaenopsis* plant.

The photograph on the first sheet (FIG. 1) is a side perspective view of a typical flowering plant of 'Fruit Punch' grown in a container.

Figure 2:
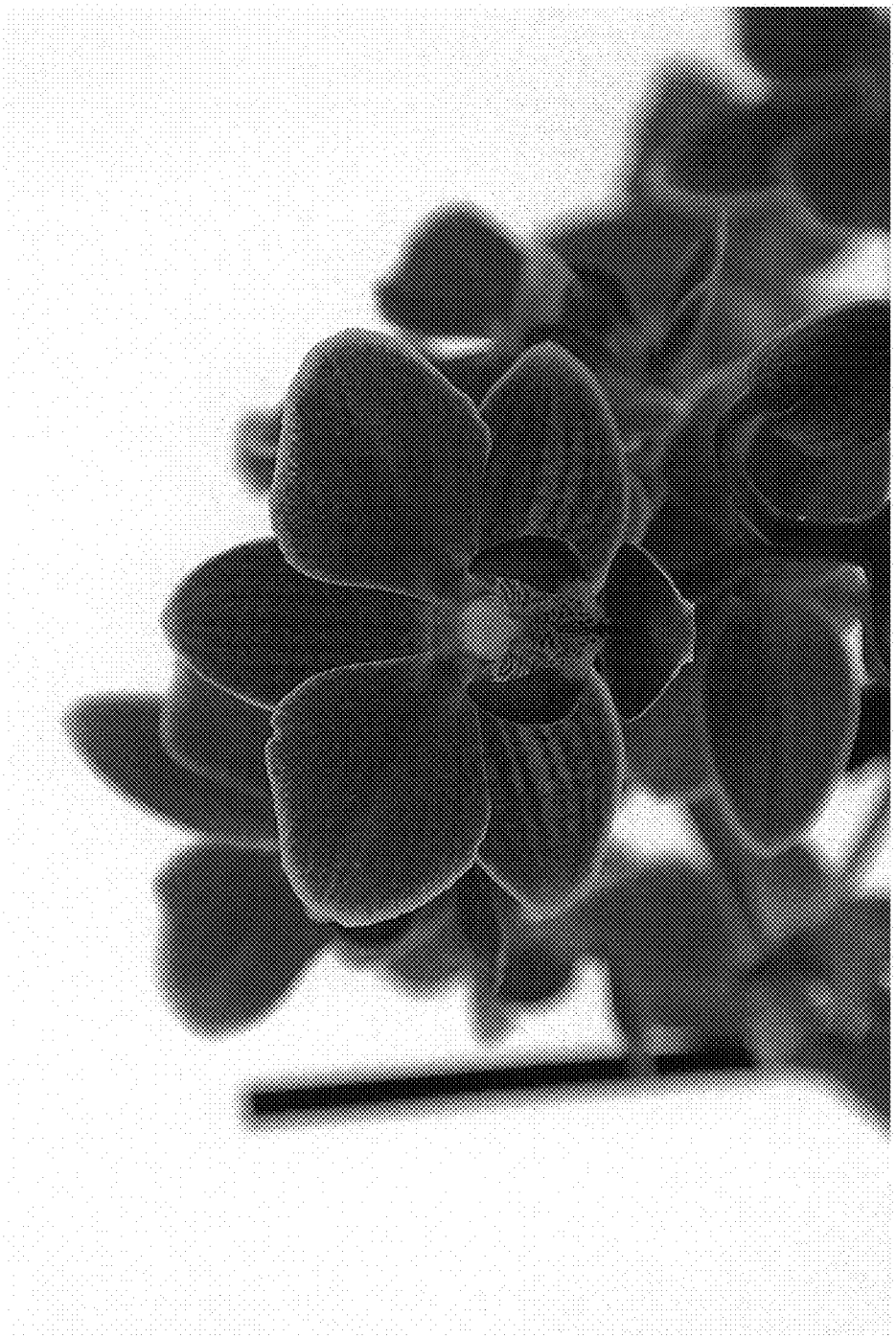

The photograph on the second sheet (FIG. 2) is a close-up view of a typical flower of 'Fruit Punch'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Doritaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: x *Doritaenopsis* (*Doritis* x *Phalaenopsis*) 'Fruit Punch'.

Parentage:

*Female parent*.—x *Doritaenopsis* (*Doritis* x *Phalaenopsis*) 'Sweet Strawberry', not patented.

*Male parent*.—x *Doritaenopsis* (*Doritis* x *Phalaenopsis*) 'Sunrise Red Peoker', not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; relatively compact and upright plant habit with typically two inflorescences per plant, each inflorescence with numerous flowers; monopodial; moderately vigorous growth habit and moderate growth rate.

*Plant height, substrate level to top of foliar plane*.—About 13.8 cm.

*Plant height, substrate level to top of inflorescences*.—About 32.8 cm.

*Plant diameter or spread*.—About 25.2 cm.

Leaf description:

*Arrangement and quantity*.—Distichous, simple; sessile; about six leaves per plant.

*Length*.—About 19.2 cm.

*Width*.—About 6.5 cm.

*Aspect*.—Outwardly arching.

*Shape*.—Oblanceolate to narrowly oblong; slightly carinate.

*Apex*.—Unequal acute to acute.

*Base*.—Sheathing. Sheath length: About 1.4 cm. Sheath width: About 1.2 cm. Sheath color: Close to 144C.

*Margin*.—Entire; slightly revolute.

*Texture and luster, upper and lower surfaces*.—Smooth, glabrous; slightly glossy.

*Venation pattern*.—Camptodromous.

*Color*.—Developing leaves, upper surface: Close to NN137B. Developing leaves, lower surface: Close to a blend of 146A and 146B; margin edges tinged with close to N200B. Fully expanded leaves, upper surface: Close to a blend of 137B and 146A; venation, close to NN137B. Fully expanded leaves, lower surface: Close to 146B; margin edges, close to NN137B; venation, close to 143A.

Inflorescence description:

*Appearance and flowering habit*.—Showy zygomorphic flowers arranged on axillary branched racemes; typically two inflorescences per plant; each inflorescence with about 25 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 21.7 cm.

*Inflorescence width*.—About 17.6 cm.

*Flower buds*.—Height: About 1.3 cm. Diameter: About 8 mm by 11 mm. Shape: Broadly ovate. Color: Center, close to 152A to 152B; towards the apex and base, close to N199A.

*Flower size*.—About 4.5 cm (vertical) by 4.9 cm (horizontal).

*Flower depth*.—About 2.5 cm.

*Petals, quantity and arrangement*.—Three, two lateral petals and one center petal transformed into a labellum.

*Lateral petals*.—Length: About 2.5 cm. Width: About 2.3 cm. Shape: Rhomboidal to broadly ovate. Apex: Obtuse to shallowly retuse. Margin: Entire. Texture and luster, upper and lower surfaces: Smooth, glabrous, velvety; matte. Color: When opening, upper surface: Close to 187D; towards the apex, close to N78A; margin edges, close to 150A; venation, close to 187D. When opening, lower surface: Close to a blend of 152D and 160A; towards the margins, close to 182B, and margin edges, close to 150A. Fully opened, upper surface: Close to 64A; towards the apex, close to 64B; margin edges, close to 151D; venation, slightly darker than 64A; color does not change with subsequent development. Fully opened, lower surface: Close to 75D; towards the margins, close to 185C to 185D; margin edges, close to 151D; color does not change with subsequent development.

*Labella*.—Appearance: Three-parted with two lateral lobes and a central lobe. Length, lateral lobes: About 1.2 cm. Width, lateral lobes: About 7 mm. Length, central lobe: About 2.4 cm. Width, central lobe: About 4 mm to 14 mm. Shape, lateral lobes: Obovate; convex. Shape, central lobe: Obovate. Apex, lateral lobes: Rounded. Apex, central lobe: Truncate. Margins, lateral and central lobes: Entire. Texture and luster, upper and lower surfaces: Smooth, glabrous, moderately velvety; matte. Callosities: Located at the base of the labellum and attachment point of the lateral petals; about 4 mm in length, about 3 mm in width and about 2 mm in height. Color: When opening, upper surface: Lateral lobes: Close to a blend of 183B and 187B; at the base, close to 159D tinged with close to 160C with dots, close to 187B. Central lobe: Close to 183A; towards the apex, close to 187D; towards the margins, close to 9B and 84D; at the base (at column connection), close to 157D with radial stripes, close to 187D. Callosities: Close to 12B with fine dots, close to 187D. When opening, lower surface: Lateral lobes: Close to 183D; towards the apex, close to 187C and 187D; at the base, close to 156B. Central lobe: Close to 151A and 151B; towards the apex, close to 76C and 76D; towards the margins, close to 183A; at the base (at column connection), close to 157A. Fully opened, upper surface: Lateral lobes: Close to 184B; at the base, close to 159D tinged with close to 160C with dots, close to 187B. Central lobe: Close to 183A; towards the apex, close to 187D; towards the margins, close to 9B and 84D; at the base (at column connection), close to 157D with radial stripes, close to 187D. Callosities: Close to 12A with fine dots, close to 187D. Fully opened, lower surface: Lateral lobes: Close to 183D; towards the apex, close to 187C and 187D; at the base, close to 156B. Central lobe: Close to 151B; towards the apex, close to 76C and 76D; at the base (at column connection), close to 157C; central lobe margin edges, close to 183A.

*Sepals*.—Quantity and arrangement: Three, one upper dorsal sepal and two lower lateral sepals. Length, dorsal sepal: About 2.7 cm. Width, dorsal sepal: About 2.7 cm. Length, lateral sepals: About 2.6 cm. Width, lateral sepals: About 2.7 cm. Shape, dorsal sepal: Elliptic to slightly obovate. Shape, lateral sepals: Ovate. Apex, dorsal and lateral sepals: Acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to 187C; venation, close to 187B; margin edges, close to 150C. When opening, lower surface: Close to 152D; towards the margins, tinged with close to 183C; margin edges, close to 151D. Fully opened, upper surface: Close to 61A; towards the base, tinged with close to N78B; venation, close to a blend of 59A and 61A; margin edges, close to 150D. Fully opened, lower surface: Close to a blend of 157A and 196B; towards the margins, close to 182B and 182C; margin edges, close to 150D. Color, lateral sepals: When opening, upper surface: Distally, close to 184B with venation, close to 187B to 187C; proximally, close to 151C with venation, close to 184A and 187C; margin edges, close to 150C. When opening, lower surface: Close to 152D; towards the margins, slightly tinged with close to 183C; margin edges, close to 151D. Fully opened, upper surface: Distally, close to 61A tinged with close to 150D with venation, close to 187D; proximally, close to 150D with venation, close to 187D; margin edges, close to 150C to 150D. Fully opened, lower surface: Close to a blend of 157A and 196B; towards the margins, slightly tinged with close to 182B and 182C; margin edges, close to 150D.

*Peduncles*.—Length: About 33.6 cm. Diameter: About 4.5 mm. Strength: Strong. Aspect: Upright to outwardly arching. Texture and luster: Smooth, glabrous; matte. Color: Close to 146A densely covered with fine dots, close to 200A.

*Pedicels*.—Length: About 2.7 cm. Diameter: About 3 mm. Strength: Moderately strong. Aspect: About 60° from peduncle axis. Texture and luster: Smooth, glabrous; matte. Color: Close to 148A; distally, close to N170D.

*Reproductive organs*.—Androecium: Column length: About 9 mm. Column width: About 5 mm. Column color: Close to N75A and N75B; distal blotch, close to 76D. Pollinia quantity: Two. Pollinia diameter (per two pollinia): About 2 mm. Pollinia color: Close to 21B. Gynoecium: Stigma length: About 3 mm. Stigma width: About 4 mm. Stigma shape: Reniform. Stigma color: Close to N155B. Ovary length: About 8 mm. Ovary diameter: About 1 mm. Ovary color: Close to 150D. Seeds and fruits: To date, seed and fruit development have not been observed on plants of the new *Doritaenopsis*.

Pathogen & pest resistance: To date, plants of the new *Doritaenopsis* have not been shown to be resistant to pathogens and pests common to *Doritaenopsis* plants.

Temperature tolerance: Plants of the new *Doritaenopsis* have been observed to tolerate temperatures ranging from about 15° C. to about 40° C. and are suitable for USDA Hardiness Zones 10 to 12.

It is claimed:

1. A new and distinct *Doritaenopsis* plant named 'Fruit Punch' as illustrated and described.

* * * * *